(12) United States Patent
Griffith

(10) Patent No.: US 8,275,462 B1
(45) Date of Patent: Sep. 25, 2012

(54) INTEGRATED PHASE-SHIFT POWER CONTROL TRANSMITTER FOR USE WITH IMPLANTABLE DEVICE AND METHOD FOR USE OF THE SAME

(75) Inventor: Glen A. Griffith, Newbury Park, CA (US)

(73) Assignee: Advanced Bionics, Valencia, CA (US)

( * ) Notice: Subject to any disclaimer, the term of this patent is extended or adjusted under 35 U.S.C. 154(b) by 0 days.

(21) Appl. No.: 13/206,975

(22) Filed: Aug. 10, 2011

Related U.S. Application Data

(62) Division of application No. 11/058,848, filed on Feb. 15, 2005, now Pat. No. 8,027,732.

(51) Int. Cl.
*A61N 1/00* (2006.01)
(52) U.S. Cl. ............... 607/57; 607/55; 607/59
(58) Field of Classification Search ......... 607/55, 607/57, 69
See application file for complete search history.

(56) References Cited

U.S. PATENT DOCUMENTS

| | | | |
|---|---|---|---|
| 4,681,111 A * | 7/1987 | Silvian | 607/59 |
| 5,876,425 A | 3/1999 | Gord et al. | |
| 6,073,050 A | 6/2000 | Griffith | |
| 6,415,186 B1 | 7/2002 | Chim et al. | |

* cited by examiner

*Primary Examiner* — Nicole F Lavert
(74) *Attorney, Agent, or Firm* — AdvantEdge Law Group, LLC

(57) ABSTRACT

Systems and methods for efficiently transmitting power using a high frequency (e.g., RF) telemetry transmitter are provided. The telemetry transmitter may include a fixed clock source (which may provide a fixed clock signal), telemetry phase shift circuitry (which may include switching circuitry and phase shifting circuitry), and a push-pull network. The telemetry phase shift circuitry generates a phase shifted clock signal that is phase shifted with respect to the fixed clock signal. The fixed and phase shifted clock signals may drive the switching circuitry to produce a high frequency signal that is passed through the push-pull network. The power or magnitude of the high frequency signal is based on the phase delay between the fixed clock signal and the phase shifted clock signal.

15 Claims, 8 Drawing Sheets

INTEGRATED PHASE-SHIFT POWER CONTROL TRANSMITTER FOR USE WITH IMPLANTABLE DEVICE AND METHOD FOR USE OF THE SAME

RELATED APPLICATIONS

The present application is a divisional application of U.S. patent application Ser. No. 11/058,848, filed Feb. 15, 2005 and issued as U.S. Pat. No. 8,027,732 on Sep. 27, 2011, the content of which is incorporated herein by reference in its entirety.

BACKGROUND INFORMATION

The present invention relates to methods and systems for controlling the power level of high frequency signals, and more particularly to RF telemetry transmitters for efficiently communicating with and powering an implanted stimulator device (e.g., an implanted cochlear stimulator (ICS)).

Cochlear implant technology is well known and has been successfully used to enable individuals to hear, whereas other hearing assist devices, such as hearing aids and head phone amplifiers, have failed. Generally, cochlear implant systems include an external unit and an implanted device. The external unit usually includes a power source (e.g., a battery), where the implanted device may not. The implanted device may receive power from the external unit by way of an inductive or radio frequency (RF) link. To transfer power from the external unit to the implanted device, the external unit and implanted device may each include a coil. Although these coils are not directly connected, a high frequency carrier signal, which is applied to the external device coil, is coupled to the implanted device coil. This coupling is akin to the flux coupling seen in transformers. That is, even though the primary and secondary windings are not directly coupled to each other, an AC signal applied to the primary winding is also applied to the secondary winding by virtue of the flux coupling. In an ICS system, the carrier signal is received by the implanted coupling and then rectified into a DC signal for powering the implanted device.

Control and/or data signals may be transmitted to the implanted device by applying a predetermined modulation signal to the carrier signal. For example, acoustic signals received and processed by the external device may be converted into electrical signals (e.g., a digital pulse stream), which may provide a basis for the modulation applied to the carrier signal.

Cochlear implant systems, like many other electronic systems, are constantly subject to ever stringent design criteria such as smaller size requirements, greater power efficiency, and lower costs. One way to address each of the foregoing design criteria, and others not mentioned, is to increase the efficiency of power conversion and transfer from the external unit to the implanted unit. Traditional power conversion and transfer techniques, although are able to provide power to the implanted device, do not completely meet the stringent criteria. As a result, the external unit of the cochlear implant systems may require bulky housings, large power requirements, and frequent replacement or charging of batteries.

One example of a known power conversion technique uses a class D, E/F, G, H, or S transmitter in combination with a voltage regulator (e.g., a switching regulator). The voltage regulator controls the transmitter supply voltage, which control is responsible for adjusting the power output of the transmitter. A drawback with this technique is that the voltage regulator requires additional circuitry such as control circuitry and discrete components such as inductors and capacitors to operate. These additional components add costs, consume additional power, and occupy extra space.

Another power conversion technique eliminates the need to use a voltage regulator to control the transmitter power output by using a pulse width modulation (PWM) technique (or duty cycle control) to adjust the magnitude of the carrier signal. One drawback of using PWM to control the transmitter power output is that both even and odd higher order harmonics may be imposed on the carrier signal. As is known in the art, harmonics represent unwanted components of a signal (e.g., a carrier signal) that are typically produced in high frequency applications. The production of both even and odd harmonics places a substantial burden on filtering circuitry because if the higher order harmonics currents are not suppressed, these harmonic currents can decrease the power efficiency of the transmitter circuitry. The production of undesirable second harmonics increases the steepness of the suppression filter circuits, which generally increases the order of the filter and the inherent losses in such filters. The radiation of the harmonic components may generate EMI (e.g., Electro-Magnetic Interference), which is often prohibited or regulated. Moreover, another drawback is that the control of the duty cycle may be difficult as it approaches zero, thus potentially preventing accurate control of power across the entire available range of power that can be transmitted on the carrier signal.

Because many cochlear implant devices are implemented in relatively small behind-the-ear units, space and power are at a premium. Furthermore, as cochlear implant devices advance, other components such as digital processing circuitry may require increased levels of power and space. Thus, there is a need for a high frequency transmitter circuit that is both compact and efficient.

SUMMARY

The present invention addresses the above and other needs by providing an efficient RF telemetry transmitter system for transmitting power and data to an implant device. The transmitter system uses a phase delay (e.g., time delay or phase shift) technique to control the power level of the signal being transmitted to the implant device. Such a technique advantageously eliminates the need of an additional voltage regulator (e.g., a switching voltage regulator) and its associated discrete components to control the voltage of the transmitted RF signal. In addition, this technique enables the transmitter to accurately control the magnitude of the RF signal to assure optimum power transfer to the implant device. Thus, the amount of power provided to the implant device can be set to a level required by the implant device. That is, an oversupply (which may result in wasted power) and an undersupply (which may result in improper implant device operation) of power to the implant device is avoided.

The transmitter circuitry according to the invention may include a carrier frequency clock source, phase shifting circuitry, switching circuitry (which may include a first and second amplifier), and a network (which may include a transformer). The transmitter circuitry, particularly the switching circuitry and the network, may be setup in a push-pull configuration. This configuration enables digital signals (e.g., a predetermined frequency clock signal and a phase delayed clock signal) to control the operation of the switching circuitry, which in turn causes signals to be applied to the network. The differential signal measured across a winding (e.g., a primary winding) of the transformer, contains the desired fundamental frequency component, as well as unwanted harmonic frequency components. The network suppress the harmonic components and passes the desired fundamental frequency as modulated in amplitude by a phase-shift summation.

In one embodiment, the switching circuitry may include a first amplifier that is responsive to a predetermined frequency clock signal to provide a first switch signal to the network (e.g., to a first node of the transformer). The switching circuitry may include a second amplifier that is responsive to a phase shifted clock signal to provide a second switch signal to the network (e.g., to a second node of the transformer). The phase shifted clock signal may be generated by the phase shifting circuitry. The phase shifted clock signal has the same frequency as the predetermined frequency clock signal, but may be shifted out of phase with respect to the predetermined frequency clock signal. For example, the phase difference between the leading edge of the phase shifted clock signal and the leading edge of the predetermined frequency clock signal circuitry may range from −180° to 0° to 180°, or in radian values −π to 0 to π.

During operation, a differential voltage exists across the transformer when the first and second switch signals are out of phase. The magnitude of the phase difference may determine the average amount of power or magnitude of power transmitted to, for example, an implant device. For example, if the phase delay is 0°, the power of the RF signal transmitted through the network may be negligible. However, as the phase delay approaches 180° or −180°, the power of the RF signal being transmitted increases, with maximum power being obtained at a 180° or −180° phase shift.

The present invention provides accurate power control over the full range (e.g., from the lowest possible order of magnitude to the highest possible order of magnitude) of potential power by adjusting the phase delay. Such adjustment of the phase delay can be done by providing a DELAY CONTROL signal to the phase shifting circuitry. For example, the magnitude (e.g., voltage level) of the DELAY CONTROL signal may determine the phase shift. The DELAY CONTROL signal may be provided by control circuitry, feedback control circuitry, or other suitable circuitry capable of providing a DELAY CONTROL signal. Moreover, such circuitry may be responsive to the power level being provided to, for example, the implant device, and may make adjustments to the DELAY CONTROL signal to ensure that an optimum power level is provided.

In one embodiment of the present invention, the network may be a double-tuned network that functions as a narrow band filter. The filter function may prevent higher order harmonics, which may be produced by the driving action of the switching circuitry, from being passed downstream of the network. In another aspect of the present invention, the switching circuitry is balanced, resulting in the production of odd harmonics, but not even harmonics. This is advantageous because it reduces the suppression filter complexity and losses as described above.

The transmitter circuitry according to the present invention may transmit data to, for example, an implant device. Data may be embedded into the predetermined frequency clock signal using a predetermined modulation scheme (e.g., ON/OFF modulation). Thus, the RF signal may provide both power and data to the implant device.

It is thus an object of the present invention to provide a compact, low power, highly efficient, RF telemetry transmitter circuit that may be used to transfer RF power from a limited power source (e.g., a small battery) through a barrier, such as the skin, to a device on the other side of the barrier (e.g., an implant device).

It is a further object of the invention to provide a compact, low power, highly efficient, RF telemetry transmitter for use within a behind-the-ear (BTE) unit of a cochlear implant system.

It is an additional object of the invention to provide a low power, highly efficient RF telemetry transmitter circuit wherein the drive level or energy content of a fixed frequency RF signal may be controlled through phase shifting of a predetermined frequency clock signal.

It is further still an object of the invention to provide a transmitter circuit that accurately provides power at practically any level ranging from a minimum power level to a maximum power level.

It is yet another object of the invention to provide a transmitter circuit that does not impose both even and odd harmonics on the carrier signal.

BRIEF DESCRIPTION OF THE DRAWINGS

The above and other objects and advantages of the invention will be apparent upon consideration of the following detailed description, taken in conjunction with the accompanying drawings, in which like reference characters refer to like parts throughout, and in which.

DETAILED DESCRIPTION

Figure 1A:
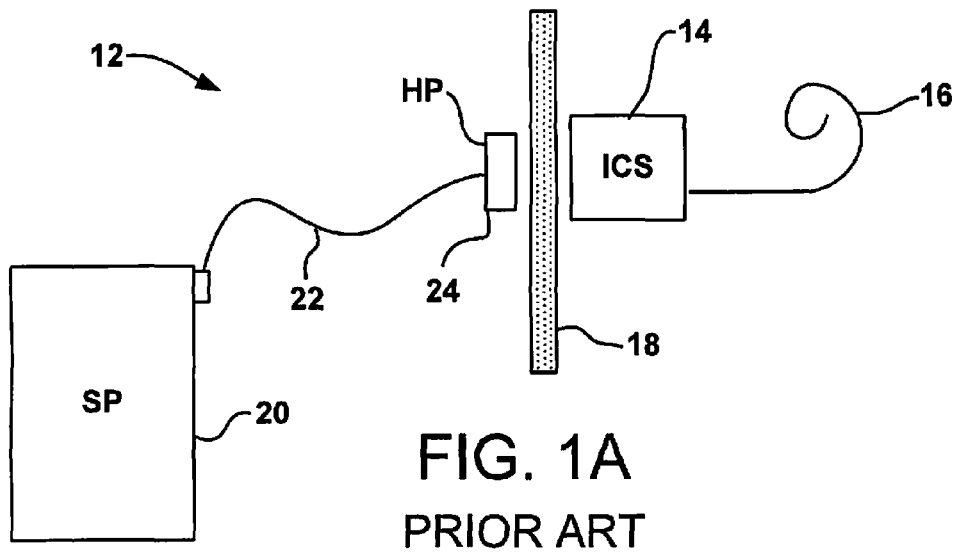
FIG. 1A shows a block diagram of a prior art ICS system.

FIG. 1A shows a representative block diagram of an ICS system 12 of the type commonly found in the prior art. A thorough description of a cochlear stimulation system of the type shown in FIG. 1A may be found, for example, in U.S. Pat. No. 5,776,172, which is incorporated herein by reference in its entirety. As seen in FIG. 1A, the ICS system 12 includes an implanted portion, including an ICS 14 and an electrode array 16, and an external portion, comprising a speech processor (SP) 20 connected to a headpiece 24 via a long cable 22. The implanted portion is separated from the external portion by a barrier such as, for example, a layer of skin 18.

Figure 1B:
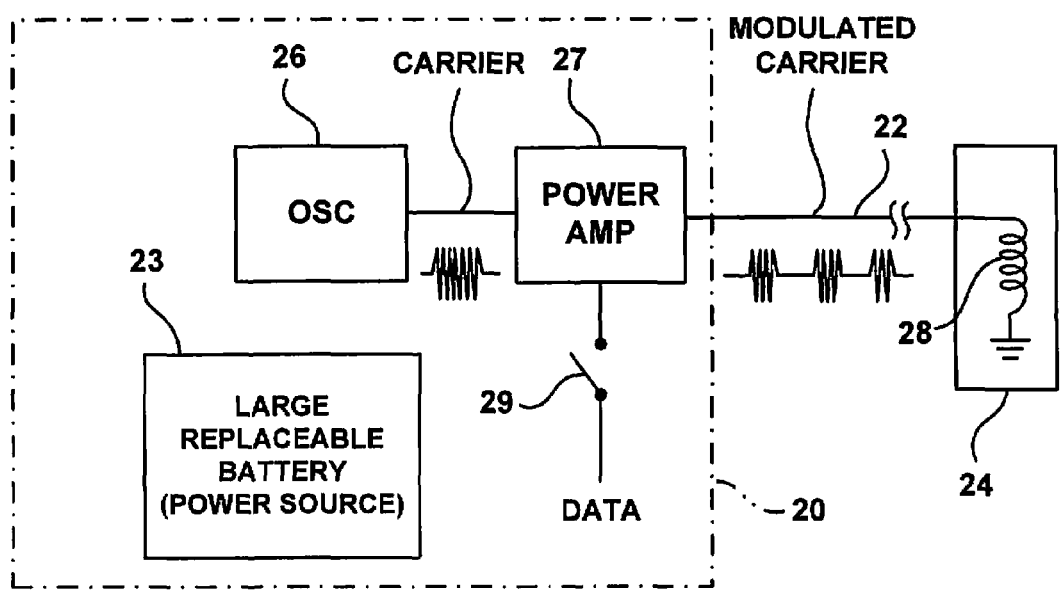
FIG. 1B shows a block diagram of a prior art transmitter modulator used in the external speech processor (SP) of the ICS system.

In operation, the prior art ICS system 12 of FIG. 1A transmits power and data through the skin barrier 18 to the implantable portion using a technique as illustrated generally in the functional block diagram of FIG. 1B. The ICS system 12 uses the received data and power to provide stimulation pulses to select electrode pairs located along the electrode array 16, as is known in the art. The SP 20, as seen in FIG. 1B, includes an oscillator 26 that generates a carrier signal which is applied to a power amplifier 27. The power amplifier is modulated with data through, for example, an ON/OFF modulation switch 29, and the resulting modulated amplified signal is sent to the headpiece 24 over the long cable 22, from which location it is transmitted to the implantable part through an antenna coil 28 housed within the headpiece 24.

Included within the SP 20 is a large replaceable battery 23, or other large power source. Such a large power source 23 is needed because the transmission scheme shown in FIG. 1B is not very efficient. That is, the power amplifier 27 is designed to amplify a sinusoidal signal, and as is readily known in the art, the amplification of sinusoidal signals is generally not an efficient process. This is because in order to amplify the sinusoidal signal without distortion, the various amplification stages, typically implemented using transistors, must operate in their linear (non-saturated) region. This means that significant amounts of power may be consumed, or lost, in the amplification stages as the amplification of the sinusoidal signal is carried out. While certain amplifier configurations may be selected in an attempt to make the sinusoidal amplification more efficient (e.g., the power amplifier 27 may be a Class C amplifier) such amplifier configurations are still not all that efficient (a Class-C amplifier typically operates at about 55% collector efficiency) and require more components (and thus more space). Fortunately, for speech processor designs of the prior art, the efficiency and size of the SP 20 were not major design concerns because the SP is simply carried by the patient (thereby allowing it to be relatively large), and a large replaceable battery 23 housed within the SP 20 could simply be replaced, when needed. (Here, the term "sinusoidal" is used to refer to a sine wave signal having little or no distortion.)

Figure 2:
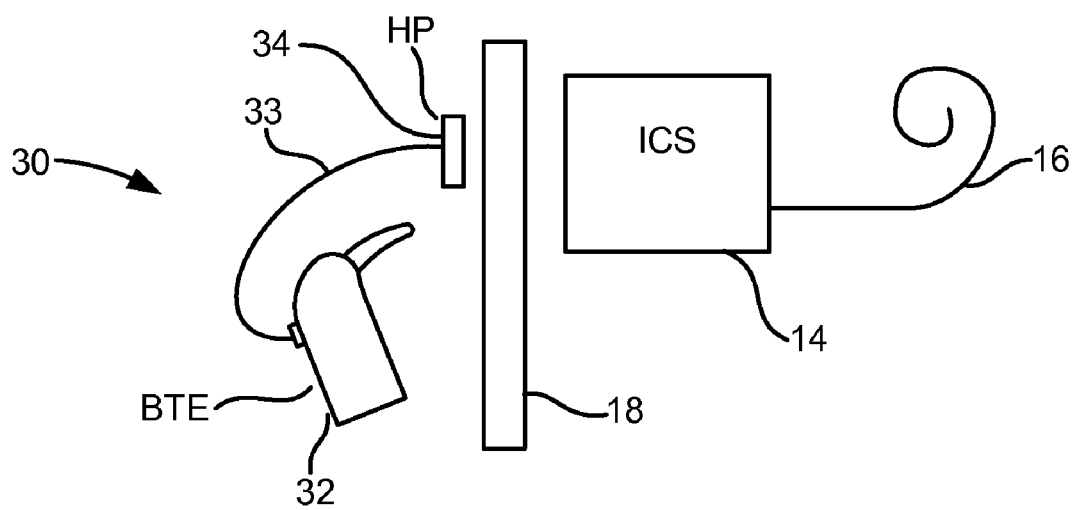
FIG. 2 shows several main components of a BTE cochlear stimulation system in which transmitter circuitry according to the principles of the present invention may be used.

FIG. 2 shows the main components of a behind-the-ear (BTE) cochlear stimulation system 30 of the type that may be used in accordance with the principles of the present invention. The implanted portion of the system 30 may include ICS system 14 and electrode array 16. The external portion of the system 30 may include a BTE unit 32 coupled to a headpiece 34 via a short cable 33. A skin barrier 18 separates the external portion from the implanted portion. The BTE unit 32 houses a speech processor, a power source, the telemetry transmitter circuit of the present invention, as well as other standard components and speech processing circuits used within an ICS system.

Headpiece 34 houses an antenna coil, and may also house (in some embodiments) a microphone. In other embodiments, the microphone may be housed within or on BTE unit 32. BTE unit 32 is designed to be worn behind the ear of its user, and the headpiece 34 is connected thereto via the short (i.e., less than two inches or so) cable 33.

Because BTE unit 32 shown in FIG. 2 is physically much smaller than is the SP unit 20 used with the prior ICS system 12 (FIG. 1A), and further because all of the circuits used within the BTE system 30 must perform substantially the same functions as are performed by equivalent circuits within the prior ICS system 12, it is necessary that such circuits perform their respective functions much more efficiently (i.e., by consuming less power than their prior art counterparts) because the power source used within the BTE system 30 cannot be as large, and hence cannot generally have the same capacity as, the power source used within the prior SP unit 20. While improved power sources (batteries) may be used in the BTE system 20 that provide a higher energy density, and hence more power in a smaller space or volume than has heretofore been achievable, it is still necessary that the circuits of the BTE system be designed with compactness and maximum efficiency in mind.

To that end, the present invention provides a highly efficient, compact, telemetry transmitter circuit for use in transmitting a high frequency carrier signal across a barrier to a remote receiver (e.g., to an implanted receiver). Such an efficient, compact telemetry transmitter circuit, and related components, is illustrated in the block diagram shown in FIG. 3.

The high frequency carrier signal may be the signal that is transmitted to implanted ICS 14 across skin barrier 18. As will be referred to herein, the magnitude or amplitude of this high frequency carrier signal may indicate the quantity of power being transmitted to the implanted ICS 14. Moreover, as will also be described herein, the high frequency carrier signal may also include data. Furthermore, the high frequency carrier signal may be referred to herein as an RF signal, a high frequency signal, or a sinusoidal signal.

Figure 3:
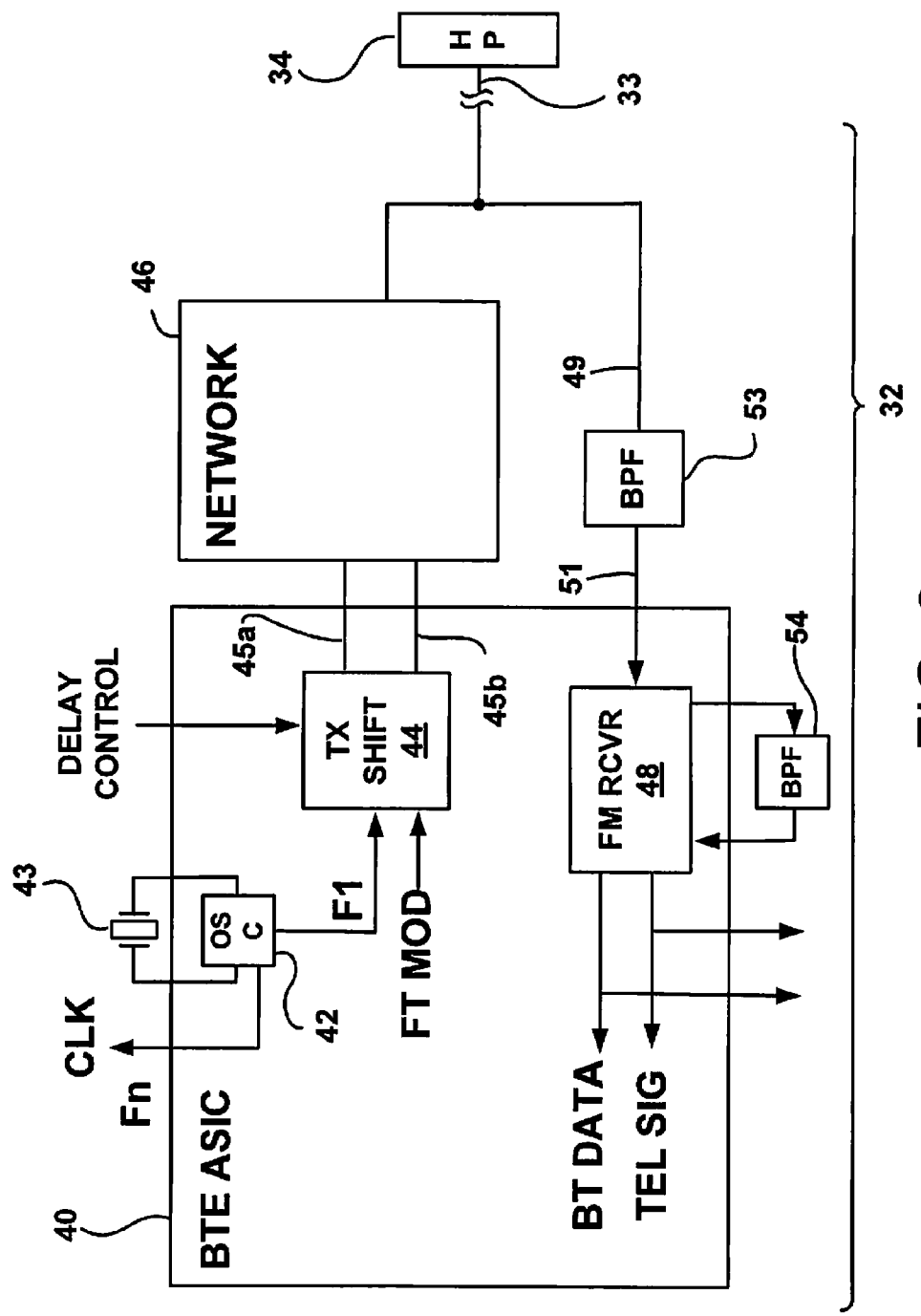
FIG. 3 shows a block diagram of transmitter circuitry and other components that may be housed within the BTE housing of a BTE cochlear stimulation system according to the principles of the present invention.

As seen in FIG. 3, the transmitter circuit may include an oscillator circuit (OSC) 42 that generates a primary clock signal having a frequency F1. For example, the clock signal frequency F1 may be 49 MHz. The OSC 42 may also generate other clock signals such as a second clock signal Fn, having a frequency that is the same as or derived from the frequency F1 of the primary clock signal. For example, the second clock signal may have a frequency of 24.5 MHz, or ½ that of the primary clock signal.

It will be understood by those skilled in the art that the present invention may be use varying frequencies and is not limited to using just one particular frequency. For example, the transmitter circuit may include clock generation circuitry that provides a clock signal that varies within a predetermined range of frequencies. Such range of frequencies may be suitable, for example, for narrow band modulation, frequency modulation, amplitude modulation, or any other suitable type of modulation.

Figure 4:
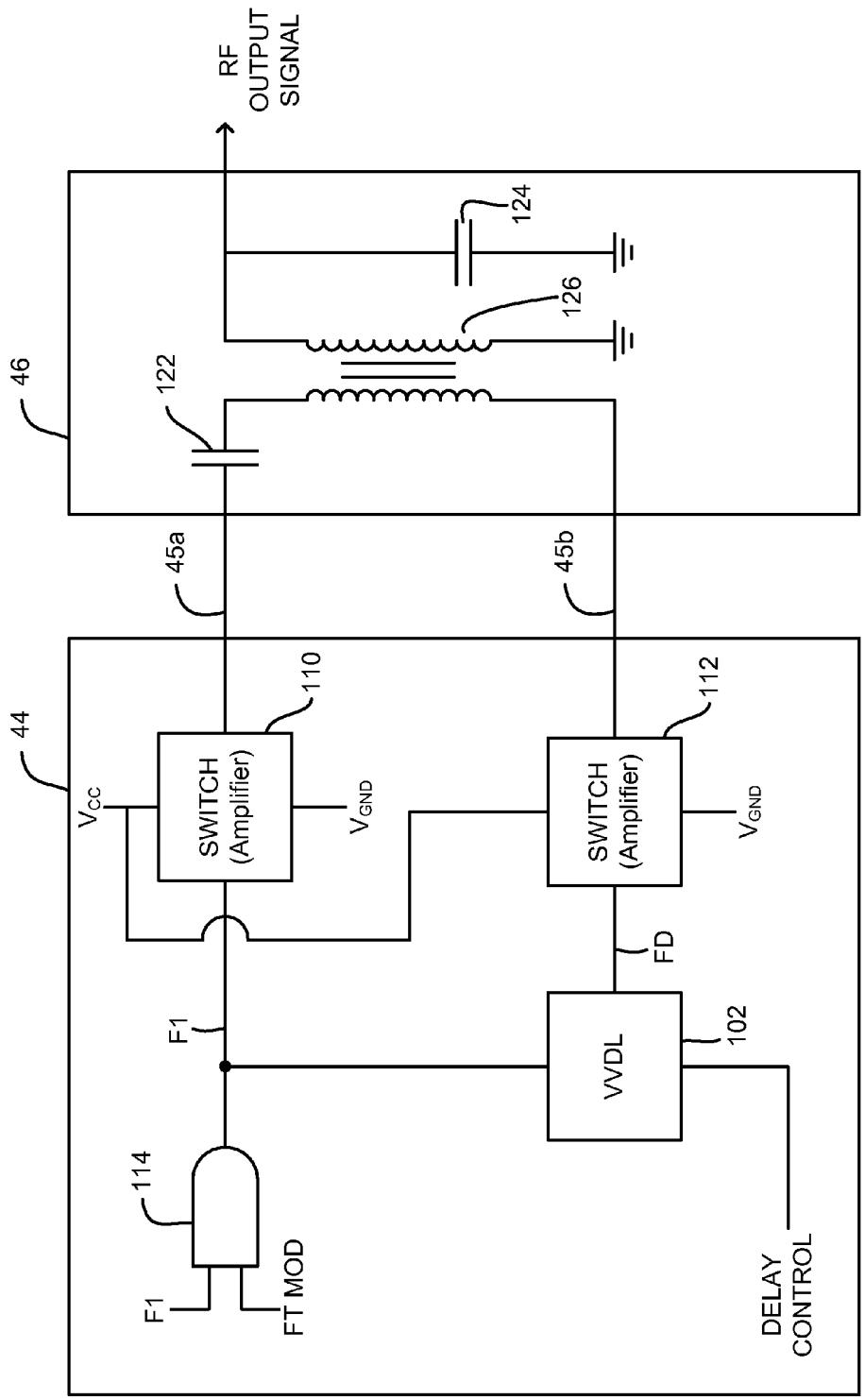
FIG. 4 shows a schematic of transmitter circuitry according to the principles of the present invention.

The primary clock signal is applied to a telemetry phase shifting circuit (TX SHIFT) 44 where it may be converted into a phase shifted clock signal based on a DELAY CONTROL signal and where it may also be modulated with a data signal, referred to in FIGS. 3 and 4 as the FT MOD signal. TX SHIFT 44 may derive its operating power from the power source, referred to as VCC, of the BTE unit. TX SHIFT 44 may provide two signals (which may be referred to as the first and second switch signals) to network 46 over lines 45a and 45b. The application of these signals to network 46 may result in a push-pull mode of operation. One signal (e.g., the second switch signal) may be phase shifted with respect to the other signal (e.g., the first switch signal) based on the DELAY CONTROL signal. These signals, when applied to network 46, produce an RF output signal, on signal line 33, including a sinusoidal signal having an amplitude that varies as a function of the phase shift between the first and second switch signals. Furthermore, the RF output signal may be modulated with data in a selected fashion as a function of the FT MOD signal. The RF output signal may then be applied to an antenna coil within the headpiece 34, where it is transmitted or coupled as a forward carrier signal, through the barrier 18 to a remote receiver (e.g., ICS 14).

The power level of the RF output signal may be selected or adjusted, as required, to assume various values by controlling the DELAY CONTROL signal. As explained more fully below, control over the power level of the signal provided to the implant device is made more efficient by selecting the phase delay of the second switch signal with respect to the first switch signal to be "just right", not too small (which may result in improper operation of the implant device), and not too large (which may result in the implant device being over-driven, and would thus represent a waste of energy).

Headpiece 34 may also include an antenna coil tuned to receive a backtelemetry signal from the implanted receiver or device. In some embodiments, in order to simplify the design of BTE unit 20, the back telemetry feature may be omitted. When used, such a backtelemetry signal is modulated with data from the ICS 14, and is typically at a different carrier frequency than is the forward carrier signal transmitted to the implanted receiver. For example, in one embodiment, where the forward carrier signal operates at a fixed frequency of 49 MHz, the backtelemetry signal may have a fixed carrier frequency of 10.7 MHz. An example of one type of modulation used to modulate the backtelemetry signal may be frequency modulation (FM), but other types of modulation can also be used.

The backtelemetry signal may be routed through a separate network (not shown) and applied to a first bandpass filter circuit (BPF) 53 over signal line 49. The filtered backtelemetry signal is then directed, over signal path 51, to an FM receiver circuit (FM RCVR) 48. FM RCVR 48 detects and demodulates the signal it receives over signal line 51. Typically, FM RCVR 48 may utilize a second BPF 54 to aid in the detection and demodulation process. As a result of such demodulation, two signals are generated by FM RCVR 48 and presented to the other circuits within BTE unit 32. Such two other signals include a data signal (BT DATA) that represents the demodulated data received through the backtelemetry signal, and a signal (TEL SIG) that identifies the presence of a backtelemetry signal within the FM RCVR 48. The presence of the TEL SIG signal may thus be used to identify that a link has been established with ICS 14. Knowing that a link has been established with an ICS may, in turn, be used for various purposes (such as a power control feedback loop). Examples of such purposes may be seen, for example, in U.S. Pat. No. 5,584,869, which is incorporated herein by reference in its entirety.

If desired, an amplifier (not shown) may be used to further control the power level of the RF output signal. Such an amplifier may receive the RF output signal from network 46 and provide an amplified variant of that signal to headpiece 34. The amplification of the RF output signal may be fixed or variable. In fixed amplification embodiments, control of the output signal amplitude may be controlled by the phase shifting circuitry. In variable amplification embodiments, control of the output signal amplitude may be controlled by one or both the phase shifting circuitry and the amplifier.

OSC 42, TX SHIFT 44, and FM RCVR 48 (when used) may all preferably be formed or embedded within the same application specific integrated circuit (ASIC) 40. Such ASIC 40 may also include the other digital circuits associated with BTE unit 22, such as the speech processing circuits and control circuitry, and hence the ASIC 40 may be referred to as the BTE ASIC. BTE ASIC 40 may be mounted on a suitable pc board (PCB) within the BTE unit 32. Other discrete components, not part of the ASIC 40, may then be mounted, as required, on the BTE PCB or otherwise housed within the BTE unit. Such other discrete components may include for example, in addition to the battery (not shown in FIG. 3), a crystal 43 used with OSC 42 to precisely control the frequency F1 of the OSC 42, network 46, and BPF 54.

FIG. 4 shows a schematic of an implementation of TX SHIFT 44 and network 46 of FIG. 3 that is in accordance with the principles of the present invention. As shown in FIG. 4, TX SHIFT 44 includes variable voltage delay line (VVDL) circuitry 102 (e.g., phase shifting circuitry), first amplifier 110, second amplifier 112, and logic circuitry 114. VVDL circuitry 102 may receive a DELAY CONTROL signal, logic circuitry 114 may receive the clock signal F1 and the FT MOD signal. Clock signal F1 may be a pulse stream operating at a predetermined clocking frequency and which pulses between a nominal voltage level (e.g., about 0 volts) and a predetermined voltage level (e.g., ±1.75 volts). The pulse may have voltage levels suitable for driving first and second amplifiers 110 and 112 HIGH and LOW.

As also shown in FIG. 4 is network 46, including transformer 126, which may receive the first and second switch signals on lines 45a and 45b, respectively and capacitors 122 and 124. Those skilled in the art will appreciate that capacitors 122 and 124 may be series-resonating capacitors that enable network 46 to operate as a double-tuned bandpass filter. Such bandpass filter advantageously eliminates the need to use additional filters downstream of network 46, thereby promoting energy transfer efficiency of the present invention.

Moreover, capacitors 122 and 124 may be used to counteract inductance of transformer 126. Additionally, capacitor 122 may prevent DC current from passing to transformer 126 and filter out harmonics produced by the driving action of amplifiers 110 and 112. Transformer 126 may be a loosely coupled transformer having a 1-to-N turns ratio, where N is an arbitrary value. Also, transformer 126 isolates amplifiers 110 and 112 from the load.

Amplifiers 110 and 112 may be driven by clock signal F1 and delayed clock signal FD, respectively, to provide the first and second switch signals to network 46. As shown in FIG. 4, amplifiers 110 and 112 are connected to a power source (e.g., VCC) and to ground. As shown in this embodiment, a single power supply is used, which reduces the number of components required. Additionally, the VCC may be the primary battery of the BTE or Speech Processor.

Amplifiers 110 and 112 may be constructed to operate as an H-bridge. As such, amplifiers 110 and 112 may each include one or more bi-directional current carrying devices (e.g., a conventional CMOS digital inverter) to provide a switching operation (e.g., where amplifiers 110 and 112 can be turned ON and OFF) to control the amplitude of the RF output signal. The power source, ground, amplifiers 110 and 112, and network 46 may form a circuit loop that sets the power level of the RF output signal according to clock signal F1 and delayed clock signal FD.

Those of skill in the art will appreciate that many different available devices can carry a bi-directional current as used in an H-bridge driver. For example, a uni-directional transistor (e.g., a bipolar transistor) that is bypassed with a diode or other circuit element may provide a bi-directional current carrying capacity. Other examples of bi-directional circuitry include insulated gate bipolar transistors and CMOS inverters.

Figure 4A:
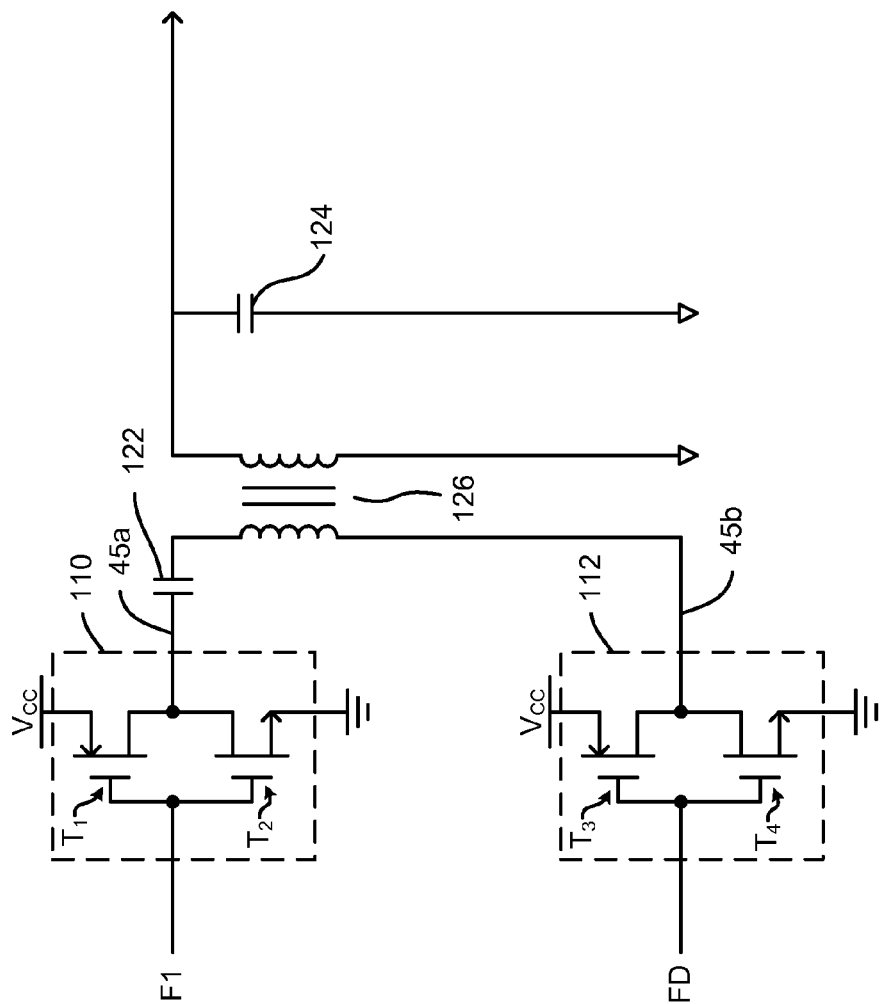
FIG. 4A shows an illustrative, but more detailed, schematic of a portion of the transmitter circuit of FIG. 4 in accordance with the principles of the present invention.

FIG. 4A shows an illustrative, but more detailed, schematic of portions of TX SHIFT 44 and network 46 of FIG. 4 in which amplifiers 110 and 112 are shown as CMOS inverters in accordance with the principles of the present invention. Each CMOS inverter may have two transistors, with one being coupled to VCC and the other being coupled to ground. These four transistors, labeled T1, T2, T3 and T4, may form a driver configuration (e.g., an H-bridge) where network 46, particularly the primary winding of transformer 126, is treated as a "load." Several different circuit paths exist depending on the states of F1 and FD. For example, when F1 is HIGH and FD is LOW, current from VCC of amplifier 112 may be routed through transformer 126 to ground of amplifier 110. When F1 and FD are both HIGH, the respective ends of the primary winding of transformer are coupled to ground via T2 and T4. When F1 and FD are both LOW, the respective ends of the primary winding of transformer 126 are both coupled to VCC via T1 and T3.

Figure 5:
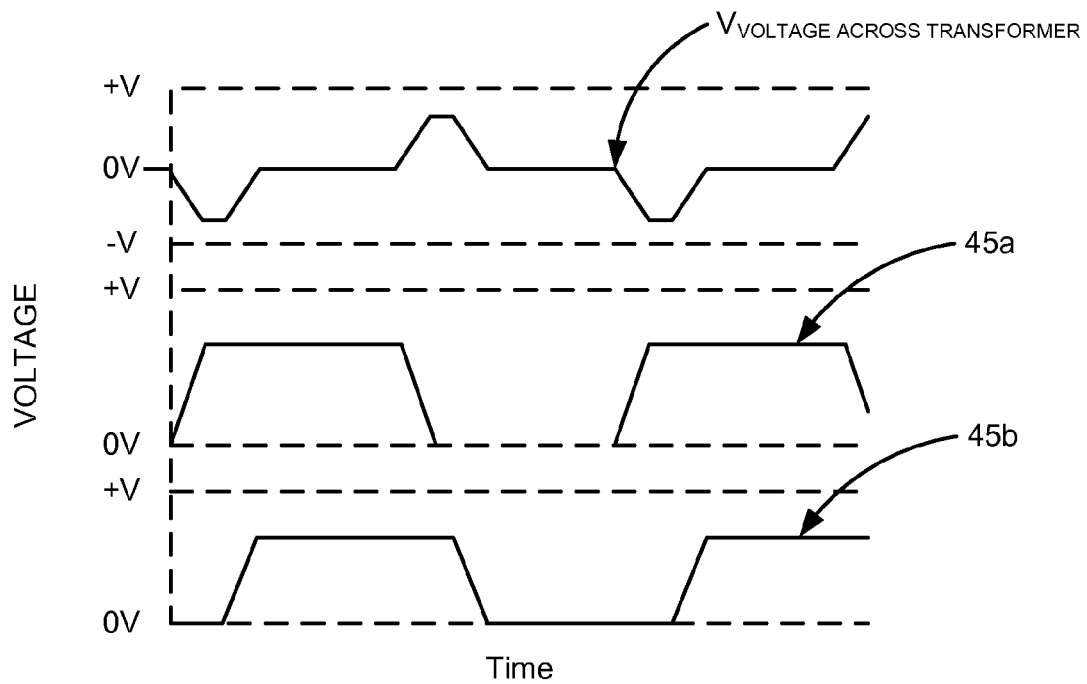
FIG. 5 shows several timing waveforms of that may be generated in the circuitry of FIG. 4 in accordance with the principles of the present invention.

To facilitate the discussion of how the power level of the RF output signal is controlled, reference will be made to FIGS. 5, 6, and 7. As stated above, TX SHIFT 44 provides the first and second switch signals on lines 45a and 45b to network 46. An example of the first and second switch signals as applied to lines 45a and 45b is shown in FIG. 5. The combination of the first and second switch signals may at given times within a clock cycle result in the application of a differential signal across transformer 126 of network 46 (as shown in FIG. 5). This differential signal may be the result of a voltage difference of the first and second switch signals at transformer 126, which sets the power level of the RF output signal.

In accordance with the present invention, a differential voltage may exist across transformer 126 when amplifiers 110 and 112 are providing signals in opposite states; that is one amplifier provides a HIGH signal and the other provides a LOW signal. As shown in FIG. 5, when line 45a is HIGH (e.g., because amplifier 110 is being driven HIGH) and line 45b is LOW (e.g., because amplifier 112 is being drive LOW), a differential voltage (shown as the triangular portion of the waveform) may exist across transformer 126. A differential voltage may not exist across transformer 126 when amplifiers 110 and 112 output signals in the same state (e.g., both HIGH or LOW). This is shown in FIG. 5 when both lines 45a and 45b are in the same state. Thus, when both lines 45a and 45b are HIGH, the differential voltage is negligible, and when both lines 45a and 45b are LOW, the differential voltage is also negligible.

The differential signal may contain frequency components at the fundamental frequency of the carrier, and all odd harmonics. Even harmonics may not be present in the differential signal because of a balanced operation of amplifiers 110 and 112. That is, amplifiers 110 and 112 are balanced because they are substantially identical and symmetrically driven. Moreover, such balance or symmetric driving of the amplifiers may enable addition/subtraction of the first and second switch signals to occur in network 46.

The power level of the carrier signal is controlled by adjusting the phase shift between the second switch signal (on line 45b) and the first switch signal (on line 45a). Referring back to FIG. 4, TX SHIFT 44 may control the level of the differential voltage across transformer 126 (and consequently the amplitude of the RF output signal) by selectively phase shifting clock signal F1. VVDL 102 may phase shift clock signal F1 based on the DELAY CONTROL signal to produce delayed clock signal FD, which drives amplifier 112. The extent to which clock signal F1 is delayed may be proportional to the voltage level of the DELAY CONTROL signal applied to VVDL 102. Thus, depending on the voltage level of DELAY CONTROL signal, the delayed clock signal FD may be phase shifted anywhere from −180° to 0° to 180° with respect to clock signal F1.

Figure 6:
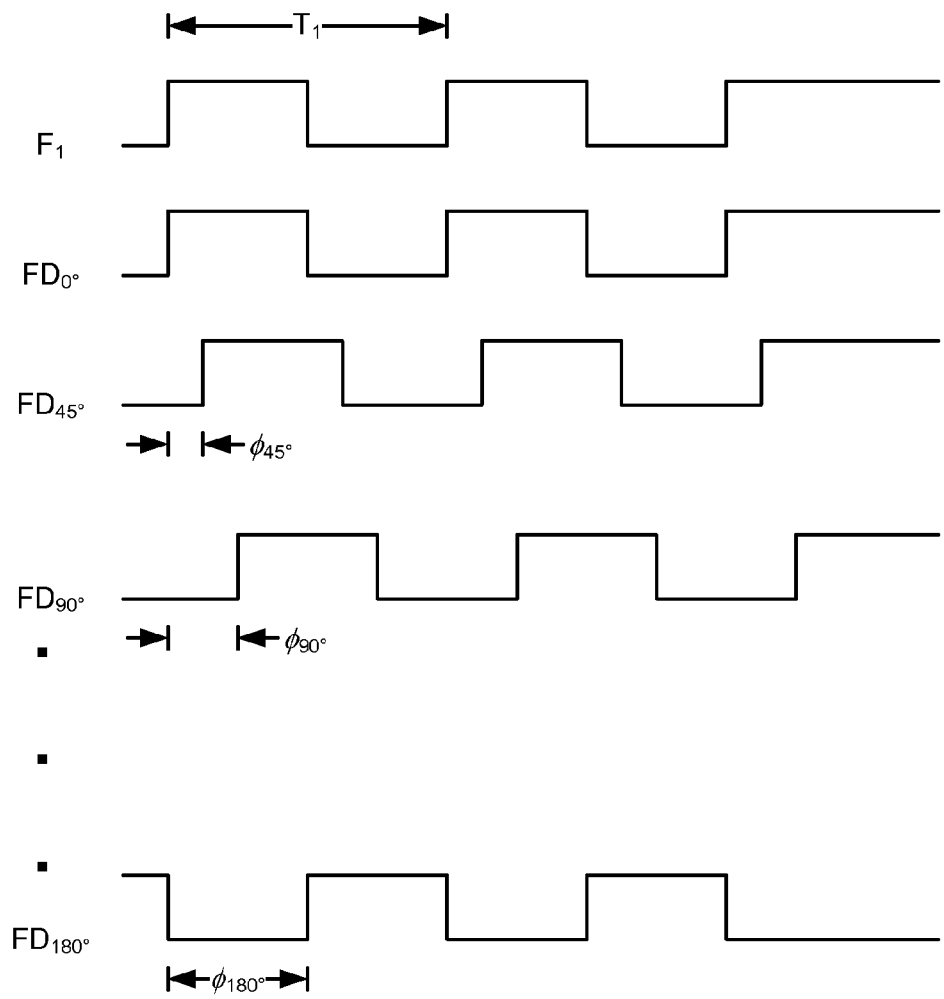
FIG. 6 shows several timing waveforms illustrating phase shifting in accordance with the principles of the present invention.
Figure 7:
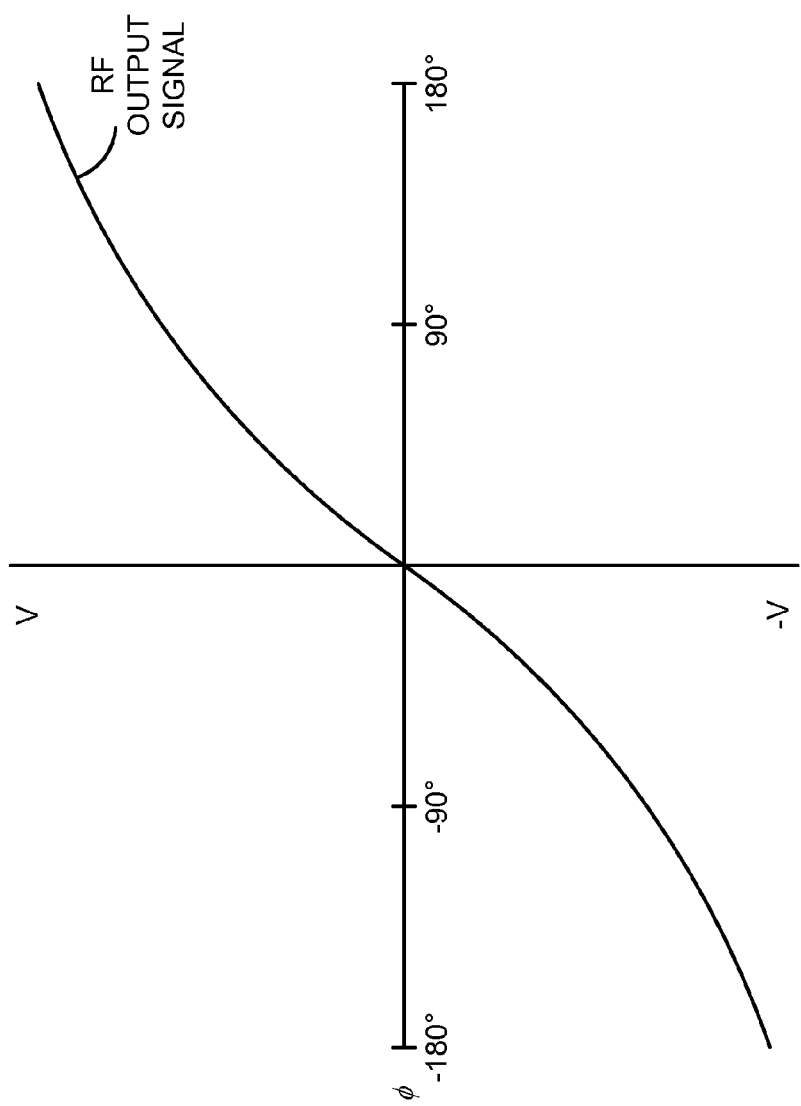
FIG. 7 shows a graph of a signal in which the magnitude varies as a function of phase delay in accordance with the principles of the present invention.

To better explain how phase shifting is implemented in accordance with the principles of the present invention to control the amplitude of the RF output signal, reference is made to FIGS. 6 and 7. FIG. 6 shows several timing waveform diagrams in accordance with the principles of the present invention. FIG. 7 shows a graph of the amplitude of the RF output signal as a function of phase shift in accordance with the principles of the present invention.

Referring now to FIG. 6, the top waveform represents the clock signal F1, having a cycle period of T1. Note that the period T1 is the inverse of the clock signal F1 (i.e., T1=1/F1). The F1 waveform may be the waveform that drives amplifier 110. The waveforms below the top waveform (the F1 waveform) represent waveforms of phase shifted clock signals and may represent a waveform that drives amplifier 112. These phase shifted waveforms are denoted as $FD_N$, where N is an angular value ranging −180° to 180°. Note that radian values ranging −π to π may be used, as IF is equivalent to an angular value of 180°. Further note that only waveforms corresponding to positive angular values are shown in FIG. 6 to avoid overcrowding the FIG., even though both positive and negative angular values are shown in FIG. 7. FIG. 6 shows that the phase shift of the various waveforms is denoted as $\phi N$, where N represents an angular value.

The $FD_{0°}$ waveform represents a time delayed clock signal having a phase delay of 0°. As shown in FIG. 6, the leading edge of $FD_{0°}$ is substantially co-linear with the leading edge of F1. Thus, $FD_{0°}$ is substantially the same as F1 at $\phi_{0°}$. Moreover, when the phase delay is 0°, the differential voltage across transformer may be negligible or about 0 volts, resulting in negligible power being carried by the RF output signal, as shown in FIG. 7. Note that when the phase delay is 0°, both amplifiers 110 and 112 provide signals in the same state (e.g., both HIGH or LOW) for the entire duration of the clock period.

The waveform $FD_{180°}$ represents a phase shifted clock signal having a phase delay of 180°. As shown in FIG. 6, the leading edge of $FD_{180°}$ is delayed by $\phi_{180°}$ with respect to the leading edge of F1. Such a delay may result in a maximum power level (or amplitude) for the RF output signal (shown in FIG. 7) because the average differential voltage across transformer 126 is maximized for a given clock period. The average voltage across transformer 126 may be maximized because the output of amplifiers 110 and 112 are in opposite states for the entire duration of the clock period.

The $FD_{0°}$ and the $FD_{180°}$ waveforms may represent the extreme ends of phase shifting in accordance with the invention, and thus correspond to the minimum and maximum power levels of the RF output signal. The other waveforms (e.g., $FD_{45°}$ and $FD_{90°}$) represent time delayed clock signals having phase delays ranging between 0° and 180°. It will be understood that by varying the phase delay to a value between 0° and 180° practically any desired power level (or amplitude) can be obtained for the RF output signal.

Several advantages of using TX SHIFT 44 are realized over the prior art. One advantage is that the maximum magnitude of power transmitted to the load is greater than the maximum magnitude of power that can be delivered by, for example, a single-ended network, with all other relevant factors (e.g., battery voltage level) being equal. For example, the push-pull mode of operation of the present invention can deliver up to 6 db more power than a single-ended network given the same load impedance and power supply, VCC. Moreover, prior-art single-ended networks require voltage regulator circuitry (e.g., a variable voltage regulator or switching regulator) with discrete components that must be added external to the integrated circuit containing the transmitter digital circuits, whereas the present invention eliminates the need for such additional discrete components.

An advantage realized in a push-pull mode of operation of operation is that amplifiers 110 and 112 are balanced. That is, the driving action of amplifiers 110 and 112 may result in the production of odd harmonics of the carrier signal, but not any even harmonics. Thus, the power efficiency is enhanced because network 46 need only filter out the higher order odd harmonics and not all higher order harmonics.

Control circuitry (not shown) may provide the DELAY CONTROL signal and FT MOD signal to TX SHIFT 44 and may receive the BT DATA and TEL SIG signals (as discussed above in connection with FIG. 3). The control circuitry may provide a DELAY CONTROL signal of an appropriate level (e.g., voltage level) to control the phase shift of FD, thereby controlling the magnitude of power transmitted on the RF output signal to the implanted ICS 14. The level of the DELAY CONTROL signal may be based on, for example, the received TEL SIG or BT DATA signal. Moreover, the level of the DELAY CONTROL signal may be such that just the right quantity of power is supplied to the implanted ICS 14.

Figure 8:
FIG. 8 illustrates one manner in which the carrier signal may be modulated with digital data in accordance with the principles of the present invention.

The FT MOD signal, which may contain data representing audio signals received by BTE unit 32, may be incorporated into the carrier signal being transmitted to the implanted ICS 14. FIG. 8 depicts one manner in which the carrier clock signal F1 may be modulated with digital data using ON/OFF keying. For example, if FT MOD and F1 are fed to logic circuitry 116 (e.g., an AND gate), the data in the FT MOD data stream can be used to modulate the carrier signal, F1. In accordance with such a modulation scheme, a stream of bit periods, of mT1 seconds each, are provided in which the carrier signal data pulses are present or not present, where m is the number of data pulses included in each bit period, and the time interval between successive data pulses is T1 seconds. Thus, for example, if T1 is equal to 20 nanoseconds, and m is equal to 10, then each bit period is 10*20=200 nanoseconds, or 0.20 µsec (where "µsec" stands for microseconds). The data scheme shown in FIG. 8 assumes that a digital "1" is represented by the presence of a burst of pulses during the data bit time, and that a digital "0" is represented by the absence of a burst of pulses during the data bit time. (This assignment, of course, could just as easily be reversed, with a digital "0" being represented by the presence of the data pulses, and a digital "1" being represented by the absence of the data pulses.) Thus, the data stream shown in FIG. 8 is representative of a digital data sequence: "10101101101 . . . "

Such a digital data sequence may, in turn, be encoded using a suitable encoding scheme, as is known in the art, to create a sequence of digital data words at a desired Baud rate.

It will be understood that the present invention is not limited to the foregoing technique for incorporating data into the carrier signal. For example, other techniques such as frequency modulation can be used.

While the application of the transmitter circuitry of the present invention is described primarily in the context of a cochlear stimulation system (e.g., an BTE cochlear stimulation system), those with skill in the art will appreciate that the present invention may be applied to any type of system that requires generation of high frequency RF signals that are transmitted at minimal power consumption.

Thus it is seen that the present invention provides a compact, low power, highly efficient, RF telemetry transmitter circuit that may be used to transfer RF power from a limited power source (e.g., a small battery) through a barrier, such as the skin, to a device on the other side of the barrier (e.g., an implant device). It is further seen that such invention finds particular applicability for use within a behind-the-ear unit of a cochlear implant system. It is also seen that the invention provides a way to control the drive level of a fixed frequency RF carrier signal by phase shifting a fixed frequency carrier input signal. A person skilled in the art will appreciate that the present invention can be practiced by other than the described embodiments, which are presented for purposes of illustration rather than of limitation, and the present invention is limited only by the claims which follow.

What is claimed is:

1. A method comprising:
providing, by a radio frequency (RF) telemetry transmitter included in a cochlear implant system, a clock signal;
generating, by the RF telemetry transmitter, a phase shifted clock signal that is phase shifted relative to the clock signal by a predetermined phase delay that is set by a delay control signal;
generating, by the RF telemetry transmitter based on the clock signal and the phase shifted clock signal, a first switch signal and a second switch signal, the second switch signal being phase shifted relative to the first switch signal by the predetermined phase delay;
generating, by the RF telemetry transmitter based on the first and second switch signals, an output signal to be transmitted to an implantable receiver circuit included within the cochlear implant system, the output signal containing power and data; and
adjusting, by the RF telemetry transmitter, a power level of the output signal in response to an adjustment in the predetermined phase delay.

2. The method of claim 1, further comprising transmitting, by the RF telemetry transmitter, the output signal to the implantable receiver circuit.

3. The method of claim 1, wherein the output signal comprises a carrier signal.

4. The method of claim 1, wherein the predetermined phase delay ranges from −180° to 180°.

5. The method of claim 1, further comprising providing, by the RF telemetry transmitter, a modulation signal for incorporating the data into the output signal.

6. The method of claim 1, wherein the clock signal comprises a variable frequency signal.

7. The method of claim 1, wherein the clock signal comprises a fixed frequency signal.

8. The method of claim 1, further comprising generating, by the cochlear implant system, stimulation current in accordance with the data contained within the output signal.

9. The method of claim 1, wherein the adjusting of the power level of the output signal comprises increasing the power level of the output signal in response to an increase in the predetermined phase delay.

10. The method of claim 1, wherein the adjusting of the power level of the output signal comprises decreasing the power level of the output signal in response to a decrease in the predetermined phase delay.

11. A method comprising:
generating, by a radio frequency (RF) telemetry transmitter included in a cochlear implant system, a first switch signal and a second switch signal, the second switch signal being phase shifted relative to the first switch signal by a predetermined phase delay that is set by a delay control signal;
generating, by the RF telemetry transmitter, a carrier signal in accordance with the first and second switch signals;
adjusting, by the RF telemetry transmitter, a power level of the carrier signal in response to an adjustment in the predetermined phase delay; and
transmitting, by the RF telemetry transmitter, the carrier signal to an implantable receiver circuit included in the cochlear implant system.

12. The method of claim 11, wherein the adjusting of the power level of the carrier signal comprises increasing the power level of the carrier signal in response to an increase in the predetermined phase delay.

13. The method of claim 11, wherein the adjusting of the power level of the carrier signal comprises decreasing the power level of the carrier signal in response to a decrease in the predetermined phase delay.

14. The method of claim 1, further comprising filtering out, by the RF telemetry transmitter, higher order harmonics of the output signal while passing a fundamental frequency of the output signal.

15. The method of claim 11, further comprising filtering out, by the RF telemetry transmitter, higher order harmonics of the carrier signal while passing a fundamental frequency of the carrier signal.

* * * * *